United States Patent [19]

Banks

[11] Patent Number: 5,473,065

[45] Date of Patent: Dec. 5, 1995

[54] FLUORINATED DIAZABICYCLOALKANE DERIVATIVES

[75] Inventor: Ronald E. Banks, Stockport, England

[73] Assignee: Air Products and Chemicals, Inc., Allentown, Pa.

[21] Appl. No.: 163,257

[22] Filed: Dec. 7, 1993

[51] Int. Cl.$^6$ .................. C07D 487/08; C07D 245/04
[52] U.S. Cl. ............... 540/472; 544/351; 540/556; 540/465; 540/541
[58] Field of Search ................. 544/351, 225, 544/226, 229; 540/472, 556, 465, 541

[56] References Cited

U.S. PATENT DOCUMENTS

| 4,935,519 | 6/1990 | Van Der Puy et al. | 546/13 |
| 5,086,178 | 2/1992 | Banks | 544/351 |

FOREIGN PATENT DOCUMENTS 0204535 12/1986 European Pat. Off. .

OTHER PUBLICATIONS

J. M. Van Paasschen et al. (Can. J. Chem. 1975, 53, 723–726).
J. M. Van Paasschen et al. (J. Inorg. Nucl. Chem. 1976, 38, 2322–2323).
T. Umemoto et al. (Bull. Chem. Soc. Jpn. 1991, 64, 1081–1092).
R. E. Banks et al., J. Chem. Soc., Chem. Commun. 1992, 595–596).

Primary Examiner—John M. Ford
Attorney, Agent, or Firm—Keith D. Gourley

[57] ABSTRACT

The present invention relates to novel N,N'-difluorinated diazabicycloalkane derivatives which are useful as electrophilic fluorinating agents, processes for preparing such N,N'-difluorinated diazabicycloalkane derivatives and methods of using such compounds as fluorinating agents. The invention also presents novel N-fluorinated azaazoniabicycloalkane-Lewis acid adduct intermediates which are formed in the processes for preparing such N,N'-difluorinated diazabicycloalkane derivatives.

16 Claims, No Drawings

FLUORINATED DIAZABICYCLOALKANE DERIVATIVES

FIELD OF THE INVENTION

The present invention relates to novel N,N'-difluorinated diazabicycloalkane derivatives which are useful as electrophilic fluorinating agents, processes for preparing such N,N'-difluorinated diazabicycloalkane derivatives and methods of using such compounds as fluorinating agents. The invention also presents novel N-fluorinated azaazoniabicycloalkane-Lewis acid adduct intermediates which are formed in the processes for preparing such N,N'-difluorinated diazabicycloalkane derivatives.

BACKGROUND OF THE INVENTION

Industry is searching for fluorinating agents which are site-selective towards organic, especially carbanionic, substrates, especially for use in preparing pharmacologically active compounds. A number of such electrophilic fluorinating agents are known but, until recently were limited in their commercial utility because such agents were expensive, hazardous, inconvenient to handle, unstable and/or insufficiently selective for general use.

U.S. Pat. No. 5,086,178 discloses N-fluorinated diazabicycloalkane derivatives which are stable, effective electrophilic fluorinating agents represented by the following Formula A:

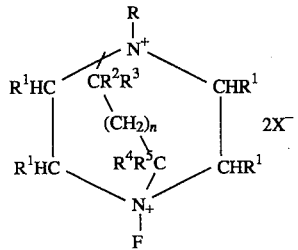

(A)

wherein n represents 0, 1 or 2;

R represents a quaternizing organic group;

each $R^1$, $R^2$, $R^3$, $R^4$ and $R^5$ independently represents hydrogen, $C_1$–$C_6$ alkyl, aryl, $C_1$–$C_6$ alkyl-substituted aryl or aryl-substituted $C_1$–$C_6$ alkyl; and each $X^-$ independently represents a counterion or $2X^-$ represents a single divalent counterion.

U.S. Pat. No. 5,086,178 discloses a process for preparing the compounds of Formula I (see Detailed Description of the Invention) wherein the corresponding N-substituted diazabicycloalkane derivative of the following Formula B are fluorinated to reach the enumerated compositions.

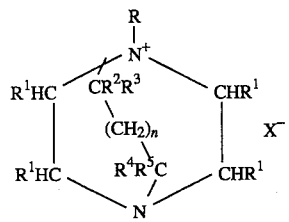

(B)

wherein n, R, $R^1$ to $R^5$, and $X^-$ are as defined above.

When fluoride is not required as a counterion in the N-substituted diazabicycloalkane derivative of Formula I, fluorination is conducted in the presence of an alkali metal salt to provide the required counterion or an alkali metal salt is added to the fluorination product in a separate step to replace the fluoride ion. However, this procedure involves forming an alkali metal fluoride by-product and the product is difficult to free from the resulting $F^-$ and adventitious $HF_2^-$ ions. Further, a substantial quantity of organic solvent, usually acetonitrile, is required in order to avoid co-precipitation of the product.

It was unexpectedly found that these problems could be overcome by addition of a readily fluorinatable Lewis acid prior to, during, or after the fluorination step. The term "readily fluorinatable Lewis acid" means a Lewis acid (Y) which readily combines with $F^-$ to form $YF^-$ and includes adducts of the free Lewis acid, such as those derived from amines or from ethers. This improved process is the subject of copending U.S. patent application Ser. No. 07/973,437 filed 11th Nov. 1992.

When the Lewis acid is added prior to fluorination, a novel azaazoniabicycloalkane-Lewis acid adduct of the following Formula C is formed as an isolatable intermediate:

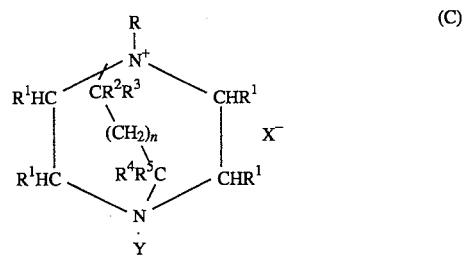

(C)

wherein n, R, $R^1$ to $R^5$, and n are as defined above and Y is a readily fluorinatable Lewis acid.

1,4-Diazabicyclo[2.2.2]octane (otherwise tetra-ethylenediamine, TEDA) is commercially available under, for example, the Trade Mark DABCO (Air Products and Chemicals Inc.) for use in the manufacture of urethane foams, elastomers and coatings, epoxy resins, and the like articles. N,N-Tetrahalo-1,4-diazabicyclo[2.2.2]-octanes in which the halogen is chlorine, bromine or iodine are known and can readily be prepared from 1,4-diaza-bicyclo[2.2.2] octane by, for example, treatment with the halogen in carbon tetrachloride. However, the corresponding tetrafluoro compound is unknown and cannot be prepared in an analogous manner. Attempts to fluorinate 1,4-diazabicyclo[2.2.2]octane with fluorine to produce 1,4-difluoro-1,4-diazoniabicyclo[2.2.2]octane difluoride gave an unidentified white solid which showed some fluorinating capacity but readily decomposed at ambient temperature into a coloured material having no electrophilic fluorinating power.

J. M. Van Paasschen et al. (Can. J. Chem. 1975, 53, 723–726) discloses, inter alia, the preparation of triethylenediamine trifluoromonoborane by reaction of triethylenediamine with trimethylamine-trifluoroborane.

J. M. Van Paasschen et al. (J. Inorg. Nucl. Chem. 1976, 38, 2322–2323) discloses, inter alia, the preparation of quinuclidine-trifluoromonoborane (1-azabicyclo[2.2.2.]-octane-trifluoromonoborane) by treating quinuclidine with trimethylaminetrifluoroborane.

EP-A-0204535 (published 10th Dec. 1986) discloses, inter alia, the preparation of N-fluoropyridinium salts by reaction of optionally substituted pyridine with fluorine and a Lewis acid. In the exemplified processes, a mixture of fluorine and nitrogen was passed through a solution of pyridine or substituted pyridine in acetonitrile and the Lewis acid subsequently added (Examples 41–44) or through a solution of both substituted pyridine and the Lewis acid (Example 45).

T. Umemoto et al. (Bull. Chem. Soc. Jpn. 1991, 64, 1081–1092) also discloses, inter alia, the preparation of N-fluoropyridinium salts by said processes of EP-A-0204535. They report that fluorination of pyridine-BF$_3$ complex yielded only trace amounts of N-fluoropyridinium tetra-fluoroborate but that fluorination of 3,5-dichloro- and pentachloro- pyridine-BF$_3$ complexes provided the corresponding tetrafluoroborate in substantial yields (79% and 87% respectively). It appears that it was necessary to use trifluoroacetic acid as the solvent when preparing N-fluoropentachloropyridinium tetrafluoroborate. Trifluoroacetic acid is not usually used as a solvent and is substantially more expensive and more difficult to remove from the product than acetonitrile.

U.S. Pat. No. 4,935,519 discloses that, contrary to the teachings of EP-A0204535 and of T. Umemoto et al. (supra), the fluorination of pyridine-BF$_3$ complex by passing a fluorine/nitrogen mixture through a solution thereof in acetonitrile, preferably containing water, yields N-fluoropyridinium pyridine heptafluorodiborate. However, it is believed that the product actually is N-fluoropyridinium pyridinium tetrafluoroborate trifluorohydroxyborate (see ref. 10 of R. E. Banks et al., J. Chem. Soc., Chem. Commun. 1992, 595–596).

The present invention provides additional effective electrophilic fluorinating agents which are readily obtainable from starting materials which are presently commercially available in substantial quantities.

SUMMARY OF THE INVENTION

Applicant has discovered that if an adduct with a readily fluorinatable moiety is formed at one or both nitrogen atoms of 1,4-diazabicyclo[2.2.2]octane, the resultant product can readily be fluorinated at one or both nitrogen atoms to provide effective electrophilic fluorinating agents. Mono- or di-adducts of other 1,4-diazabicycloalkanes can similarly be fluorinated to provide electrophilic fluorinating agents. Further, Applicant has discovered that 1,4-difluoro-1,4-diazabicycloalkanes also can be prepared by fluorinating the corresponding 1,4-bis(trialkylsilyl)-1,4-diazoniabicycloalkane salts.

DETAILED DESCRIPTION OF THE INVENTION

According to a first aspect of the present invention, there are provided N,N'-difluorinated diazabicycloalkane derivatives of the following Formula I

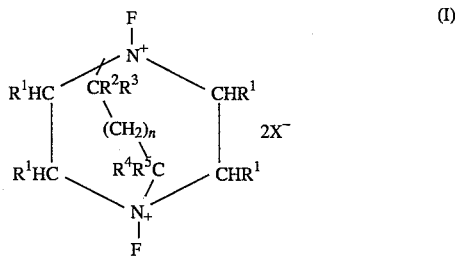

wherein
n represents 0, 1 or 2;
each R$^1$, R$^2$, R$^3$, R$^4$ and R$^5$ independently represents hydrogen, C$_1$–C$_6$ alkyl, aryl, C$_1$–C$_6$ alkyl-substituted aryl or aryl-substituted C$_1$–C$_6$ alkyl; and each X$^-$ represents a counterion or 2X$^-$ represents a single divalent counterion.

According to another embodiment of the present invention, N-fluorinated azaazoniabicycloalkane -Lewis acid adducts of the following Formula II are presented:

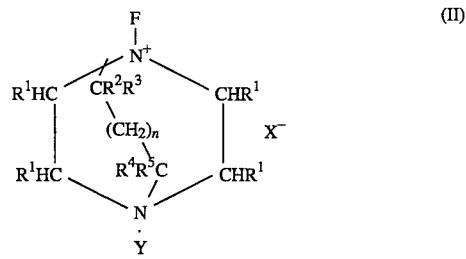

wherein
n represents 0, 1 or 2;
each R$^1$, R$^2$, R$^3$, R$^4$ and R$^5$ independently represents hydrogen, C$_1$–C$_6$ alkyl, aryl, C$_1$–C$_6$ alkyl-substituted aryl or aryl-substituted C$_1$–C$_6$ alkyl; each X$^-$ represents a counterion.; and Y represents a readily fluorinatable Lewis acid.

When any of R$^1$ to R$^5$ in Formulae I or II is other than hydrogen, it is preferably benzyl, phenyl or, especially, C$_1$–C$_4$ alkyl, particularly methyl. Usually no more than one R$^1$ at the 2 and 3 ring positions and no more than one R$^1$ at the 5 and 6 ring positions will be other than hydrogen. Preferably, all R$^1$ are hydrogen and usually no more than one of R$^2$, R$^3$, R$^4$ and R$^5$ is other than hydrogen. Preferably, all of R$^2$ to R$^5$ are hydrogen.

Most preferably, n is 0 and each R$_1$ is hydrogen (ie. the compounds of Formula I are derivatives of 1,4-diazabicyclo [2.2.2]octane). Thus, according to a preferred embodiment, the N,N'-fluorinated 1,4-diazabicyclo[2.2.2]octane derivatives of Formula I are of the following Formula III

wherein X$^-$ is as defined above, and the preferred N-fluorinated azaazoniabicycloalkane-Lewis acid adducts of Formula II are of the following Formula IV:

wherein X$^-$ and Y also are as defined above.

The counterion represented by X$^-$ in Formulae I to IV can be any anion which can be a counterion to the quaternizing fluorine. Usually, but not necessarily, the counterion will be weakly nucleophilic. When the relevant compound is a compound of Formula I or III prepared from an diazabicycloalkane-Lewis acid adduct (see later) or is a compound of Formula II or IV, the counterion usually will be derived from the Lewis acid (i.e. X$^-$=YF$^-$).

Suitable anions include halides, especially fluoride (F$^-$); fluorosulfate (SO$_3$F$^-$); alkanesulfonates, especially methanesulfonate (CH$_3$SO$_3^-$); alkyl sulfates, especially methyl sulphate (CH$_3$SO$_4^-$); perfluoroalkanesulfonates, preferably triflate (CF$_3$SO$_3^-$) and nonaflate (C$_4$F$_9$SO$_3^-$); arenesulfonates, especially tosylate (ie. p-toluene-sulfonate; CH$_3$C$_6$H$_4$SO$_3^-$); alkanecarboxylates; perfluoroalkanecarboxylates; tetrafluoroborate (BF$_4^-$); tetraphenylborate (Ph$_4$B$^-$); hexafluorophosphate (PF$_6^-$); hexafluoroantimonate (SbF$_6^-$); chlorate (ClO$_3^-$); and sulfate (SO$_4^-$=2X$^-$). The preferred anions are fluoride, triflate, tosylate and, especially, tetrafluoroborate.

The counterion represented by YF⁻ and the moiety Y in Formulae II and IV are derived from a free readily fluorinatable Lewis acid (Y) or an adduct thereof. The term "readily fluorinatable Lewis acid" means a Lewis acid (Y) which readily combines with F⁻ to form YF⁻ and includes adducts of the free Lewis acid, such as those derived from amines or from ethers. The adduct moiety can be any which is inert under the reaction conditions in the sense that it does not prevent the required reaction from proceeding. Suitably, the adduct is derived from an amine, especially trimethylamine, or from an ether, especially diethyl ether. The Lewis acid can be a perfluorinated Lewis acid of the formula $ML_m$ (wherein M is a Lewis acid-forming element; each L is fluorine, perfluoroalkyl or perfluoroaryl; and m is the valency of M) or any other Lewis acid (Y) which readily combines with F⁻ to form YF⁻ without complicating side reactions. Usually M will be a metal or metalloid of Group IIIA, IVB, VA, VB or VIA of the Periodic Table. Suitable Lewis acids include aluminum trifluoride, antimony pentafluoride, arsenic pentafluoride, boron trifluoride, tris(trifluoromethyl)-boron, tris(trifluorophenyl)boron, niobium pentafluoride, phosphorus pentafluoride, selenium trioxide, sulfur trioxide, tantalum pentafluoride, tellurium hexafluoride, titanium tetra fluoride, vanadium pentafluoride, and zirconium tetrafluoride. Presently, phosphorus penta-fluoride, sulfur trioxide and, especially, boron tri-fluoride are preferred.

Preparation of the compounds of Formulae I and II will be described hereinafter with reference to the respective 1,4-diazabicyclo[2.2.2]octane derivatives but it will be appreciated that the remaining compounds of said Formulae can be prepared from analogous reactants. Some of the relevant reaction sequences can be represented as follows:

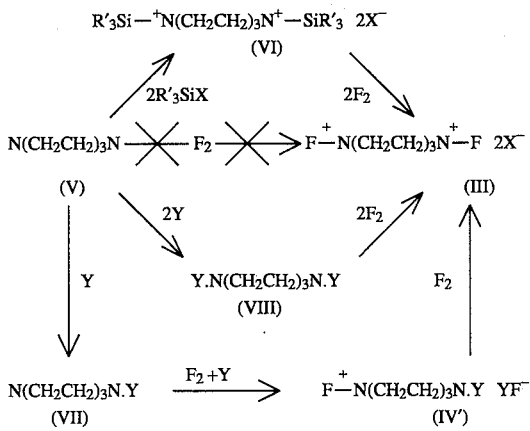

wherein R' is a $C_1$–$C_6$ alkyl group, X corresponds to the counterion X⁻ and, when the relevant compound is formed by fluorination of a Lewis acid adduct, X⁻ is YF⁻.

Analogous compounds to 1,4-diazabicyclo[2.2.2]octane (V) in which the ring carbon atoms are substituted by $R^1$ to $R^5$ (as defined above) and/or there are one or two additional carbon atoms in the bridging chain of the formula IX:

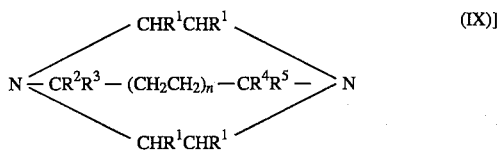

are known per se or can be prepared by analogous methods to those known per se. In particular, those compounds of Formula IX in which n is 0 can be obtained by acid-catalyzed ring closure of the corresponding N-(hydroxyethyl)piperazine. The N-(hydroxyethyl) piperazines can be obtained by reaction of the corresponding piperazine with ethylene oxide or an appropriately substituted ethylene oxide. Substituted piperazine reactants can be obtained by reaction of an ethanolamine, an ethylene oxide and ammonia with the ethanolamine and/or ethylene oxide being appropriately substituted. The diazabicyclononane derivatives in which n is 1 or 2 can be obtained by treatment of the corresponding piperazine or homopiperazine with an appropriate alkyl dihalide.

The fluorination processes of the present invention are usually carried out using a stirred-tank batch reactor into which the fluorine is admitted either as a single charge of the gas at sub-atmospheric pressure or as a continuous flow of fluorine blended with nitrogen or other inert diluent at about atmospheric pressure. When fluorinating an adduct of Formula VII, an amount of the same or different Lewis acid is present to provide the counterion YF⁻ of the N-fluorinated adduct of Formula II.

In the first enumerated fluorination method, fluorine is passed into a stirred low temperature solution or suspension of the relevant intermediate (IV', VI, VII or VIII) in a suitable organic solvent, for example trichlorofluoromethane or especially acetonitrile. Usually, the temperature is in the range –35° C. to –78° C. and the fluorine pressure is below 20 mmHg (2.7 kPa). In the second enumerated fluorination method, fluorine heavily diluted with an inert gas, usually nitrogen, is passed through said solution at about ambient pressure (see U.S. Pat. Nos. 4,479,901 and 5,086,178).

Reaction conditions suitable for forming the adducts of Formulae VII and VIII depend upon the physical state of the Lewis acid. If the Lewis acid is a liquid or solid at ambient temperature, it can simply be added to a solution of 1,4-diazabicyclo[2.2.2]octane (V) in an anhydrous, preferably polar, solvent which, if a Lewis acid itself, is weaker than the Lewis acid reactant. Suitable solvents include acetonitrile, diethyl ether, and dimethyl sulfoxide. Usually, the reaction will be carried under anhydrous conditions out at –10° C. to +40° C., preferably at or about ambient temperature. If the Lewis acid is a gas at ambient temperature, it can be condensed into a cold reactor containing a solution of the 1,4-diazabicyclo-[2.2.2]octane in a said solvent and the mixture allowed to warm to, for example, ambient temperature under anaerobic conditions. Alternatively, the Lewis acid can be admitted either neat or diluted with an inert gas, for example nitrogen, to a cooled reactor containing a stirred solution of 1,4-diazabicyclo[2.2.2]octane. The temperature of the cold tube will depend upon the boiling point of the Lewis acid gas but usually will be in the range –200° C. to –100° C.

The amount of Lewis acid and other process conditions will determine whether the adduct is primarily the monoadduct of Formula VII or the di-adduct of Formula VIII.

Usually the 1,4-bis(trialkylsilyl)-1,4-diazoniabicycloalkane salts of Formula VI will not be isolated but a mixture of the corresponding 1,4-diazabicyclo[2.2.2]-octane (V) and an appropriate trimethylsilylating agent (2R'₃SiX) will be subjected to the fluorination conditions.

N,N'-Difluorinated diazabicycloalkane derivatives of Formula I and N-fluorinated azaazoniabicycloalkane-Lewis acid adducts of Formula II also can be prepared by fluorinating a corresponding 1-perfluoroalkanoyl-1,4-diazoniabicycloalkane-Lewis acid adduct (corresponding to Formula C hereinbefore in which R is perfluoroalkanoyl). Suitably, the adduct is a 1-perfluorobutyryl-1,4-diazonia-bicycloalkane-trifluoromonoborane tetrafluoroborate and the fluorination is conducted in the presence of an alkali metal tetrafluoroborate in acetonitrile under nitrogen. 1-Perfluorobutyryl-1,4-diazoniabicycloalkane-trifluoromono-borane tetrafluoroborates can readily be prepared by contacting a perfluorobutyryl halide with a 1,4-diazonia-bicycloalkane-trifluoromonoborane in the presence of sodium tetrafluoroborate in acetonitrile at low temperature.

The novel fluorinating agents of Formulae I and II are used in manner know per se as electrophilic fluorinating agents (see, for example, R. E. Banks et al J. Chem. Soc. Perkin Trans. I, 1988, 2805). The N,N'-difluorinated diazabicycloalkane derivatives appear to be unstable in the presence of moisture and hence should be protected from atmospheric moisture by, for example, storage under dry nitrogen in polyalkene or similar containers resistant to hydrogen fluoride.

The invention is illustrated by the following non-limiting Examples. $^{19}F$ NMR spectra were recorded at 188.3 MHz using trifluoroacetic acid as the external reference (positive values refer to downfield absorptions).

EXAMPLE 1

1-Fluoro-4-aza-1-azoniabicyclo[2.2.2]octane-trifluoromonoborane tetrafluoroborate

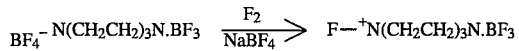

Fluorine (ca. 10 mmol) diluted with nitrogen (ca. 10% $F_2$ by volume) was bubbled slowly through a cold (ca.−35° C.) vigorously-stirred solution of 1,4-diazabicylco[2.2.2]-octane-trifluoromonoborane (see J. M. Van Paasschen and R. A. Geanangel, Can. J. Chem., 1975, 53, 723–726) (1.0 g, 5.5 mmol) and sodium tetrafluoroborate (0.6 g, 5.5 mmol) in HPLC-grade acetonitrile (100 cm$^3$). The reaction solution was filtered to remove sodium fluoride and the filtrate evaporated under reduced pressure, leaving a yellow solid; this was washed with small quantities of dry acetonitrile until it became white, recovered by filtration, dried in vacuo at ambient temperature and shown by elemental analysis and NMR to be 1-fluoro-4-aza-1-azoniabicyclo-[2.2.2]octane-trifluoromonoborane tetrafluoroborate (1.05 g, 3.7 mmol, 67%) [Found: C, 25.0; H, 4.3; N. 9.3; active F ($^+$NF), 6.6%. $C_6H_{12}B_2F_8N_2$ requires C, 25.2; H, 4.2; N, 9.8; active F, 6.7%], m.p. (decomp.) 172°–173° C., $\delta_F$ (solution in CD$_3$CN; external CF$_3$CO$_2$H reference) +125.0 (br. s; $^+$NF), −72.0 (s; BF$_3$/BF$_4^-$) p.p.m., $\delta_H$ (same soln.) 3.42 (m; 3×CH$_2$), 4.20 (br. m; 3×CH$_2$) p.p.m. (unassigned absorptions caused by impurities were present in the $^1$H spectrum). After being stored at ambient temperature in glass for a few days the sample was shown to be at least 90% pure by iodometric analysis.

EXAMPLE 2

1,4-Difluoro-1,4-diazoniabicyclo[2.2.2]octanebis-(tetrafluoroborate)

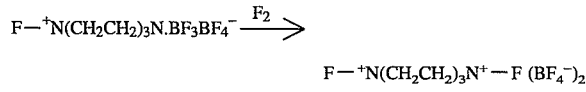

Using an apparatus and techniques employed previously to prepare N-fluoroquinuclidinium fluoride from quinuclidine and fluorine in a closed reactor (R. E. Banks, R. A. Du Boisson, W. D. Morton, and E. Tsiliopoulos, J. Chem. Soc., Perkin Trans. 1, 1988, p.2805), a cold (−35° C. stirred mixture of the 1-fluoro-4-aza-1-azoniabicyclo-[ 2.2.2]octane-trifluoromonoborane tetrafluoroborate prepared in Example 1 (0.3 g, 1.05 mmol) in dry acetonitrile (200 cm$^3$) was treated with neat fluorine [less than 20 mmHg (2.7 kPa) pressure] until consumption of fluorine became imperceptible. After unchanged fluorine had been pumped out of the reactor, the vacuum was broken with dry nitrogen and the apparatus allowed to warm to room temperature. The reaction mixture was evaporated, leaving a white solid which was washed with dry acetonitrile (2×25 cm$^3$), dried in vacuo, and shown by NMR analysis to be essentially 1,4-difluoro-1,4-diazoniabicyclo[2.2.2]octane bis(tetrafluoro-borate) (0.29 g, 0.90 mmol, 86%), $\delta_F$ (solution in CD$_3$CN; external CF$_3$CO$_2$H reference) +116.2 (s; $^+$NF), −73.0 (s; BF$_4^-$) p.p.m. (rel. int. 1:4); $\delta_H$ (same soln.) 4.72 p.p.m.

EXAMPLE 3

1,4-Difluoro-1,4-diazoniabicyclo[2.2.2]-octanebis(tetrafluoroborate)

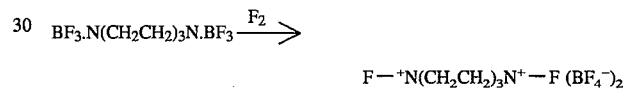

Fluorine diluted with nitrogen (ca. 10% by volume $F_2$) was bubbled slowly through a cold (−35° C.) stirred solution of 1,4-diazabicyclo[2.2.2]octanebis(trifluoromonoborane) (see H. C. Brown and B. Singaram, Inorg. Chem. 1980, 19, 455–457 & J. R. McDivitt and G. L. Humphrey, Spectrochem. Acta. Part A 1974, .30a, 1021) (1.0 g, 4.0 mmol) in dry AnalaR acetonitrile (100 cm$^3$) until the exit gas gave a strong positive test for fluorine (KI paper). As the reaction proceeded, the suspended complex dissolved. The reaction solution was evaporated under reduced pressure at ambient temperature, leaving a pale yellow solid residue. This was shaken with a small quantity of dry acetonitrile and the mixture filtered to remove traces of insoluble material; evaporation of the filtrate provided a hygroscopic white solid (0.62 g shown by NMR analysis to be 1,4-difluoro-1, 4-diazoniabicyclo[2.2.2]octane bis(tetra-fluoroborate) [$\delta_F$ (solution in CD$_3$CN; external CF$_3$CO$_2$H reference) +116.25 (s; $^+$NF), −72.83 (s; 2×BF$_4^-$);$\delta_H$ (same solution) 4.72 (br. s) p.p.m.] contaminated with 1-fluoro-4-aza- 1-azoniabicyclo [2.2.2]octane-trifluoromonoborane tetrafluoroborate and the starting material. Owing to the reactive nature of 1,4-difluoro-1,4-diazoniabicyclo[2.2.2]-octane [e.g. loss of oxidising power occurred in the presence of moisture with concomitant production of fluoride ion, a process followed by $^{19}F$ NMF analysis of a solution of the salt in D$_2$O at intervals (complete loss of the $^+$NF absorption occurred in less than 60 minutes at room temperature, leaving a spectrum comprising only F$^-$ and BF$_4^-$ absorptions at −50.2 and 72.5 p.p.m. respectively)], it was impossible to obtain an acceptable elemental analysis (Found: C, 25.8; H, 5.0; N, 11.4; BF$_4$, 49.6. Calc. for $C_6H_{12}B_2F_{10}N_2$: C, 22.2; H, 3.7; N, 8.6; BF$_4$, 53.6%) or iodometric estimation of F$^+$content (Found: 7.7%. Calc.=11.7%; oxidation of I$^-$aq. to I$_2$ occurred instantaneously at 20° C.).

EXAMPLE 4

1,4Difluoro-1,4-diazoniabicyclo[2.2.2]octanebis-(hexafluorophosphate)

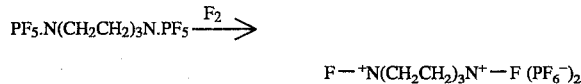

$$F-{}^+N(CH_2CH_2)_3N^+-F\ (PF_6^-)_2$$

Using the method of Example 3, a cold (−35° C.) suspension of 1,4-diazabicyclo[2.2.2]octane-bis(penta-fluorophosphorane) (0.50 g, 1.37 mmol) in acetonitrile (100 cm³) was treated with fluorine (ca. 1:10 by volume of $F_2$ in nitrogen) until the reactor exit gas gave a strong positive test for fluorine. Evaporation of the reaction mixture provided a white solid which was purified by dissolving it in dry acetonitrile (30 cm³) and adding dry diethyl ether (20 cm³) dropwise to the solution. This gave 0.54 g (1.23 mmol, 90%) of 1,4-difluoro-1,4-diazoniabicyclo[2.2.2]octane bis(hexafluorophosphate), $\delta_F$ (solution in $CD_3CN$; external $CF_3CO_2H$ reference) 116.29 (⁺NF), +5.76 (d, $PF_6^-$; $J_{PF}$ 705 Hz) p.p.m, $\delta_H$ (same soln.) 4.75 p.p.m., which reacted immediately with aqueous potassium iodide, liberating iodine, and decomposed in the presence of moisture [a solution in $D_2O$ showed no ⁺NF absorption in its ¹⁹F NMR spectrum after 5 hours, only peaks at +5.81 ($PF_6^-$) and −51.70 ($F^-$) p.p.m.].

1,4-Diazabicyclo[2.2.2]octane-bis(pentafluoro-phosphorane), which is believed to be a novel compound, was prepared from $PF_5$ (21.43 mmol) and TEDA (10.53 retool) in dry acetonitrile (50 cm³). The yellow product was purified by dissolving it in fresh acetonitrile, adding decolorising charcoal, filtering the suspension, and treating the filtrate with dry diethyl ether. This gave an 83% yield of the required complex, which was recovered by filtration, dried in vacuo, and shown to be pure by NMR analysis [$\delta_H$ 3.25 (s); $\delta_F$ +3.59 p.p.m., $J_{PF}$ 709 Hz].

EXAMPLE 5

1,4,Difluoro- 1,4-diazoniabicyclo[2.2.2]octanebis(fluorosulfate)

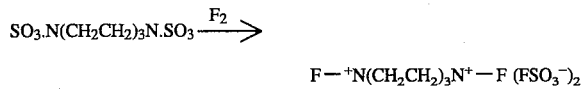

$$F-{}^+N(CH_2CH_2)_3N^+-F\ (FSO_3^-)_2$$

A 1:2 complex of 1,4-diazabicyclo[2.2.2]octane-sulfur trioxide (0.4 g) was fluorinated, as described in Example 3. The product was isolated and purified as described in Example 4 for its bis(hexafluorophosphate) analogue to provide 1,4-difluoro1,4diazoniabicyclo[2.2.2]bis(fluorosulfate) (0.45 g, 88% yield) [$\delta_F$ (fresh solution in $D_2O$; external $CF_3CO_2H$ reference) +115.0 (s; ⁺NF), −52.0 (s; F⁻ from decomposition), −73.0 (s; $FSO_3^-$), $\delta_H$ (same soln.) 4.85 (m) p.p.m.]which lost its ability to oxidise aqueous potassium iodide to iodine when dissolved in water and left overnight.

EXAMPLE 6

1,4-Difluoro-1,4-diazoniabicyclo[2.2.2]octane bistriflate

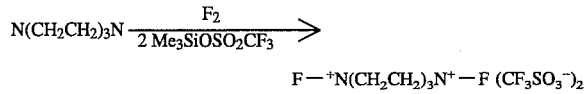

$$F-{}^+N(CH_2CH_2)_3N^+-F\ (CF_3SO_3^-)_2$$

Fluorine diluted with nitrogen (ca. 10% $F_2$ by volume) was passed through a cold (−35° C.) stirred solution prepared by mixing 1,4-diazabicyclo[2.2.2]octane (1.0 g, 8.9 mmol) and trimethylsilyl triflate (3.9 g, 17.6 mmol) in dry acetonitrile (100 cm³). When the exit gas from the reactor gave a very strong positive test for fluorine, the reaction solution was evaporated and the white solid residue obtained was dissolved in dry acetonitrile (30 cm³). Addition of dry diethyl ether to this solution caused the precipitation of 1,4-difluoro-4-diazoniabicyclo[2.2.2]-octane bistriflate (3.6 g, 8 mmol, 91%), which was dried in vacuo to give material with consistent NMR parameters [$\delta_F$ (solution in $CD_3CN$; external $CF_3CO_2H$ reference)+116.0(⁺NF), −0.9($CF_3SO_3^-$) p.p.m.; 67 $_H$ (same soln.) 4.83 p.p.m.].

EXAMPLE 7

1,4-Difluoro- 1,4-diazoniabicyclo[2.2.2]octane bis(tetrafluoroborate) and 1-Fluoro-4-aza-1-azoniabicyclo[2.2.2]octane-trifluoromonoborane tetrafluoroborate Step A
1-Heptafluoro-n-butyryl-1,4-diazoniabicyclo[2.2.2]-octane-trifluoromonoborane tetrafluoroborate

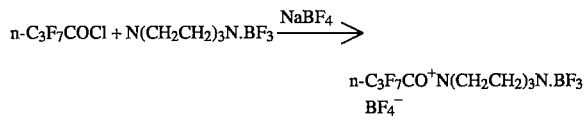

n-$C_3F_7CO^+N(CH_2CH_2)_3N.BF_3$
$BF_4^-$

Commercial heptafluoro-n-butyryl chloride (4.65 g, 20 mmol) was condensed, in vacuo, into a cold (−196° C.) Pyrex™ tube (300 cm³) containing a frozen mixture of 1,4-diazoniabicyclo[2.2.2octane-trifluoromonoborane (3.57 g, 20 mmol), sodium tetrafluoroborate (2.19 g, 20 mmol), and anhydrous acetonitrile (100 cm³). The tube was sealed (Rotaflo™ tap), allowed to warm to 20° C. and shaken mechanically for 3 days. The product was filtered to remove sodium chloride and the filtrate evaporated (Rotavapor™ ), leaving a white solid residue which was shown by elemental analysis to be impure 1-heptafluoro-n-butyryl-1,4-diazoniabicyclo[2.2.2]octane-trifluoromonoborane tetrafluoroborate [Found: C,26.6; H,2.6; F,53.9; N,6.6. $C_{10}H_{12}B_2F_{14}N_2O$ requires C, 25.9; H,2.6; F 57.4; N, 6.0%], m.p. 241°−243° C., $\delta_F$ [solution in $CD_3CN$—$(CD_3)_2SO$; external $CF_3CO_2H$ reference]−2.47 ($CF_3$),−39.29 ($CF_2$), −48.6 ($CF_2$),−70.8 ($BF_3,BF_4^-$)p.p.m.

Step B
1,4-Difluoro-1,4-diazoniabicyclo[2.2.2]octane bis(tetrafluoroborate) and 1-Fluoro-4-aza-1azoniabicyclo[2.2.21]octane-trifluoromonoborane tetrafluoroborate

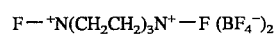

$$F-{}^+N(CH_2CH_2)_3N^+-F\ (BF_4^-)_2$$

-continued

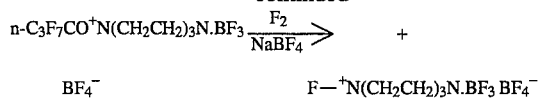

Using the method of Example 3, a cold (−40° C.) suspension of 1-heptafluoro-n-butyryl-1,4-diazoniabicyclo-[2.2.2]octane-trifluoromonoborane tetrafluoroborate, (4.0 g, 8.6 mmol) from Step A above and sodium tetrafluoroborate (0.94 g, 8.6 mmol) in dry acetonitrile (200 cm³) was treated with fluorine (ca. 1:10 by volume of $F_2$ in $N_2$) until the reactor exit gas gave a positive test for fluorine. Work-up of the product by the usual methods gave 1,4-difluoro-1,4-diazoniabicyclo[2.2.2]octane bistetrafluoroborate (1.4 g, 4.3 mmol, 50%) [Found: C, 22.2; H, 4.0; F, 58.7; N, 7.2. Calc. for $C_6H_{12}B_2F_{10}N_2$:C, 22.2; H, 3.7; F, 58.7; N, 8.7] and 1-fluoro-4-aza-1-azoniabicyclo[2.2.2]octane-trifluoromonoborane tetrafluoroborate (0.85 g, 3.0 mmol, 35%); both products gave positive tests for $N^+F$ compounds (moist KI paper) and were identified by NMR analysis ($^1H$ and $^{19}F$).

EXAMPLE 8

Fluorinations with 1-Fluoro-4-aza-1-azoniabicyclo[2.2.2]octane-trifluoromonoborane tetrafluoroborate (A) Fluorination of Anisole A mixture of anisole (i.e. methoxybenzene) (0.38 g, 3.52 mmol) and 1-fluoro-4-aza-1-azoniabicyclo[2.2.2]-octane-trifluoromonoborane tetrafluoroborate (1.0 g, 3.5 mmol) in dry acetonitrile (50 cm³) was heated at 90° C. overnight under anaerobic conditions in a glass ampoule. Dilution of the product with dry diethyl ether (50 cm³) caused the precipitation of a white solid which was removed by filtration and shown by NMR spectroscopy ($^1H$ and $^{19}F$) to be 1-hydro-4-aza-1-azoniabicyclo[2.2.2]octane-trifluoromonoborane tetrafluoroborate. The filtrate was concentrated by evaporation and shown by $^{19}F$ NMR spectroscopy and GC analysis to be a 5:3 mixture of 2-and 4-fluoroanisole (82% yield).

(B) Fluorination of Phenol

An equimolar mixture of phenol (0.1 g) and 1-fluoro-4-aza-1-azoniabicyclo[2.2.2]octane-trifluoromonoborane tetrafluoroborate (0.3 g) dissolved in dry methanol (50 cm³) was stirred overnight at room temperature to give a ca. 1:1 mixture of 2-and 4-fluorophenol in 72% yield.

EXAMPLE 9

Fluorinations with 1,4-Difluoro-1,4-diazoniabicyclo[2.2.2]octane salts (A) Fluorination of Anisole The procedure of Example 9 (A) was repeated using 0.12 g anisole and with 0.5 g of 1,4-difluoro-1,4-diazonia-bicyclo[2.2.2]octane bistriflate as the fluorinating agent to give a 1.7:1 mixture of 2-and 4-fluoroanisole in 75% yield.

When the triflate was replaced by other 1,4-difluoro-1,4diazoniabicyclo[2.2.21]octane salts the product ratios (2-fluoroanisole:4-fluoroanisole) and yields (based on anisole) were as follows:

| salt | product ratio | product yield |
|---|---|---|
| bis(tetrafluoroborate) | 1.8:1 | 62% |
| bis(hexafluorophosphate) | 1.8:1 | 68% |
| bis(fluorosulfate) | 2:1 | 47% |

(B) Fluorination of Diethyl phenylmalonate

A cold (−10° C.) solution of diethyl sodio(phenyl)-malonate in anhydrous tetrahydrofuran [prepared in conventional fashion from sodium hydride (2.5 mmol) and diethyl phenylmalonate (0.5 g, 2.1 mmol) in THF (15 cm³)] was added slowly to a cold (−10° C.) stirred solution of 1,4-difluoro-1,4-diazoniabicyclo[2.2.2]octane bistriflate (0.95 g, 2.12 mmol) in dry acetonitrile (50 cm³) under an atmosphere of nitrogen. The reaction mixture was allowed to warm to room temperature and then diluted with diethyl ether (100 cm³). The mixture was then washed with 0.5M oxalic acid (30 cm³), 10% aqueous potassium hydrogen carbonate (30 cm³), and saturated brine (30 cm³) (in that order), dried (MgSO₄), filtered, and the filtrate evaporated under reduced pressure to provide diethyl fluoro(phenyl)-malonate (65% yield) with correct NMR parameters.

As is evident from the preceding examples, the present invention provides effective electrophilic fluorinating agents which are readily obtainable from starting materials which are presently commercially available in substantial quantities.

I claim:

1. N,N'-difluorinated diazabicycloalkane derivatives represented by the formula

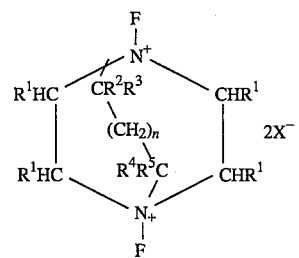

wherein n represents 0, 1 or 2;

each $R^1$, $R^2$, $R^3$, $R^4$ and $R^5$ independently represents hydrogen or a $C_1$–$C_6$ alkyl; and each $X^-$ independently represents a counterion or $2X^-$ represents a single divalent counterion.

2. The compound according to claim 1 wherein n is 0 and each $R^1$ to $R^5$ is hydrogen.

3. The compound according to claim 1 wherein $X^-$ is selected from the group consisting of fluoride; fluoro-sulfate; methanesulfonate; methyl sulfate; triflate; nonaflate; tosylate; tetrafluoroborate; tetraphenylborate; hexafluorophosphate; chlorate, and hexafluoroantimonate.

4. The compound according to claim 3 wherein $X^-$ is selected from the group consisting of tetrafluoroborate, tosylate and triflate.

5. The compound according to claim 4 wherein both $X^-$ are tetrafluoroborate.

6. N-fluorinated azazoniabicycloalkane-Lewis acid adducts represented by the formula:

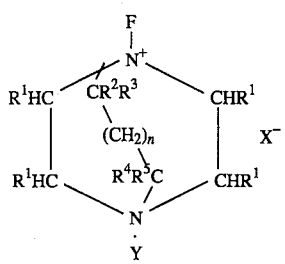

wherein n represents 0,1 or 2;

each $R^1$, $R^2R^3R^4$ and $R^5$ independently represents hydrogen or a $C_1$–$C_6$ alkyl;

each $X^-$ represents a counterion; and Y represents a readily fluorinatable Lewis acid.

7. The compound according to claim 6 wherein Y is a perfluorinated Lewis acid of the formula $ML_m$, wherein M is a metal or metalloid of Group IIIA, IVB, VA, VB or VIA of the Periodic Table; each L is fluorine, perfluoroalkyl or perfluoroaryl; and m is the valency of M.

8. The compound according to claim 6 wherein Y is selected from the group consisting of aluminum trifluoride, antimony pentafluoride, arsenic pentafluoride, boron trifluoride, tris(trifluoro-methyl)boron, tris(trifluoro-phenyl)boron, niobium penta-fluoride, phosphorus pentafluoride, selenium trioxide, sulfur trioxide, tantalum pentafluoride, tellurium hexafluoride, titanium tetrafluoride, vanadium pentafluoride, and zirconium tetrafluoride and co-ordination compounds thereof.

9. The compound according to claim 8 wherein Y is boron trifluoride.

10. The compound according to claim 6 wherein n is 0 and each $R^1$ to $R^5$ is hydrogen.

11. The compound according to claim 6 wherein $X^-$ is selected from the group consisting of fluoride; fluoro-sulfate; methanesulfonate; methyl sulfate; triflate; nonaflate; tosylate; tetrafluoroborate; tetraphenylborate; hexafluorophosphate; chlorate, and hexafluoroantimonate.

12. The compound according to claim 11 wherein $X^-$ is selected from the group consisting of tetrafluoroborate, tosylate and triflate.

13. The compound according to claim 6 wherein $X^-$ is $YF^-$ where Y is a readily fluorinatable Lewis acid.

14. The compound according to claim 13 wherein $YF^-$ is tetrafluoroborate.

15. A compound selected from the group consisting of 1,4-Difluoro-1,4-diazoniabicyclo[2.2.2]octane bis(tetrafluoroborate);

1,4-Difluoro-1,4-diazoniabicyclo[2.2.2]octane bis(tetrafluoroborate);

1,4-Difluoro-1,4-diazoniabicyclo[2.2.2]octane bis(hexafluorophosphate);

1,4-Difluoro-1,4-diazoniabicyclo[2.2.2]octane bis( fluorosulfate); and 1,4-Difluoro-1,4-diazoniabicyclo[2.2.2]octane bistriflate 16. A compound comprising 1-Fluoro-4-aza-1-azoniabicyclo[2.2.2]octane-trifluoromonoborane tetrafluoroborate.

* * * * *